United States Patent [19]

Szabadkai et al.

[11] Patent Number: 5,106,846
[45] Date of Patent: Apr. 21, 1992

[54] 2,3-THIOMORPHOLINEDIONE-2-OXIME DERIVATIVES AND PHARMACEUTICAL COMPOSITIONS CONTAINING THEM

[75] Inventors: István Szabadkai; Kálmán Harsányi, both of Budapest; Ágnes Lampert, Ajka; György Domány, Budapest; Béla Hegedüs, Budapest; Elemér Ezer, Budapest; Judit Matuz, Budapest; Katalin Sághy, Budapest; László Szporny, Budapest; György Hajós, Budapest; Krisztina Székely, Budapest, all of Hungary

[73] Assignee: Richter Gedeon Vegyeszeti Gyar RT, Budapest, Hungary

[21] Appl. No.: 477,999

[22] PCT Filed: Dec. 13, 1988

[86] PCT No.: PCT/HU88/00080

§ 371 Date: Jul. 10, 1990

§ 102(e) Date: Jul. 10, 1990

[87] PCT Pub. No.: WO89/05805

PCT Pub. Date: Jun. 29, 1989

Related U.S. Application Data

[63] Continuation of PCT/HU88/00080, Dec. 13, 1988.

[30] Foreign Application Priority Data

Dec. 14, 1987 [HU] Hungary .................. 5630/87

[51] Int. Cl.$^5$ .................. A61K 31/54; C07D 279/12
[52] U.S. Cl. .................. 514/227.5; 544/58.2
[58] Field of Search .................. 544/58.2; 514/227.5

[56] References Cited

U.S. PATENT DOCUMENTS

| 3,790,566 | 2/1974 | Bellina | 260/243 R |
|---|---|---|---|
| 3,883,510 | 5/1975 | Bellina | 260/239.3 R |
| 3,894,150 | 7/1975 | Durden, Jr. | 424/246 |
| 3,930,002 | 12/1975 | Durden, Jr. | 424/246 |
| 4,003,895 | 1/1977 | Durden, Jr. | 260/243 R |
| 4,003,897 | 1/1977 | Durden | 260/243 R |

FOREIGN PATENT DOCUMENTS

2813281 A1 3/1977 Fed. Rep. of Germany .

OTHER PUBLICATIONS

Chemical Abstracts, vol. 90, No. 11, issued Mar. 12, 1979, abstract No. 90:821-62Z, p. 172, column 1, CA 90:82162Z.

*Primary Examiner*—Patricia L. Morris
*Attorney, Agent, or Firm*—Birch, Stewart, Kolasch & Birch

[57] ABSTRACT

The present invention relates to compounds of the general formula (I),

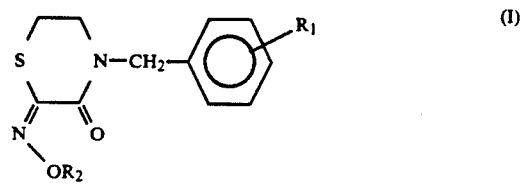

wherein
  $R_1$ stands for hydrogen, halogen, $C_{1-4}$alkyl, $C_{1-4}$alkoxy or nitro group;
  $R_2$ means a $C_{1-7}$alkyl group optionally substituted by: a hydroxyl or oxo group; or an ester group containing 1 to 4 carbon atoms in the alkoxy moiety; or a $C_{1-4}$alkoxy, cyano, amino, $C_{1-4}$alkylamino, or dialkylamino group; or an acyl group containing 1 to 7 carbon atoms in the alkyl moiety; or
  $R_2$ means an aryl-$C_{1-7}$alkyl group optionally bearing the substituents defined above for $R_2$ in the alkyl chain and optionally substituted by halogen, nitro, $C_{1-4}$alkyl or alkoxy group in the benzene ring; or
  $R_2$ represents an allyl, phenylallyl or phenylsulfonyl group, both latter groups optionally being substituted by halogen or a $C_{1-4}$alkyl group in the benzene ring; or
  $R_2$ stands for a carbamoyl group substituted by one or two $C_{1-4}$alkyl group(s) or phenyl group on the nitrogen atom.

The compounds according to the invention show a cytoprotective and acid secretion-inhibiting action and are effective against gastric and duodenal ulcers.

3 Claims, No Drawings

2,3-THIOMORPHOLINEDIONE-2-OXIME DERIVATIVES AND PHARMACEUTICAL COMPOSITIONS CONTAINING THEM

This application is a continuation of PCT/HU88/0080, filed Dec. 13, 1988.

This invention relates to novel 2,3-thiomorpolinedione-2-oxime-derivatives of the general formula (I),

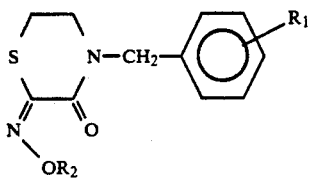

(I)

wherein
- $R_1$ stands for hydrogen, halogen, $C_{1-4}$alkyl, $C_{1-4}$alkoxy or nitro group;
- $R_2$ means a $C_{1-7}$alkyl group optionally substituted by: a hydroxyl or oxo group; or an ester group containing 1 to 4 carbon atoms in the alkoxy moiety; or a $C_{1-4}$alkoxy, cyano, amino, $C_{1-4}$alkylamino, or dialkylamino group; or an acyl group containing 1 to 7 carbon atoms in the alkyl moiety; or
- $R_2$ means an aryl-$C_{1-7}$alkyl group optionally bearing the substituents defined above for $R_2$ in the alkyl chain and optionally substituted by halogen, nitro, $C_{1-4}$alkyl or alkoxy group in the benzene ring; or
- $R_2$ represents an allyl, phenylallyl or phenylsulfonyl group, both latter groups optionally being substituted by halogen or a $C_{1-4}$alkyl group in the benzene ring; or
- $R_2$ stands for a carbamoyl group substituted by one or two $C_{1-4}$alkyl group(s) or phenyl group on the nitrogen atom as well as the pharmaceutical compositions containing these compounds.

The compounds of the general formula (I) have interesting cytoprotective and gastric acid secretion-inhibiting properties and are effective against gastric and duodenal ulcers.

The therapeutic importance of the above new compounds is very high since the number of patients suffering from gastric and duodenal ulcer is continuously increasing both in the absolute and relative sense as well. Although a number of drugs are known which are useful for the ulcer therapy, no similar effect has up to the present been described for 2,3-thiomorpholinedione-2-oximes.

According to the literature, several patents (U.S. Pat. Nos. 3,790,566, 3,883,510, 3,894,150, 3,930,002, 4,003,895 and 4,003,897) describing 2,3-thiomorpholinedione-2-oxime derivatives as pesticides were granted for the Union Carbide and the du Pont companies; however, no benzyl group substituted by $R_1$ was bound to the ring nitrogen in the compounds of these patents.

Thus, the aim of the present invention was to find novel, therapeutically useful compounds which can be prepared economically on an industrial scale, too.

Accordingly the invention relates also to a process for the preparation of the new compounds of general formula (I),

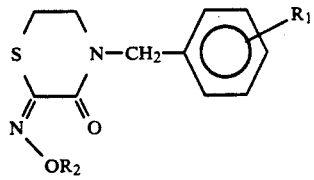

(I)

wherein
- $R_1$ stands for hydrogen, halogen, $C_{1-4}$alkyl, $C_{1-4}$alkoxy or nitro group;
- $R_2$ means a $C_{1-7}$alkyl group optionally substituted by: a hydroxyl or oxo group; or an ester group containing 1 to 4 carbon atoms in the alkoxy moiety; or a $C_{1-4}$alkoxy, cyano, amino, $C_{1-4}$alkylamino, or dialkylamino group; or an acyl group containing 1 to 7 carbon atoms in the alkyl moiety; or
- $R_2$ means an aryl-$C_{1-7}$alkyl group optionally bearing the substituents defined above for $R_2$ in the alkyl chain and optionally substituted by halogen, nitro, $C_{1-4}$alkyl or alkoxy group in the benzene ring; or
- $R_2$ represents an allyl, phenylallyl or phenylsulfonyl group, both latter groups optionally being substituted by halogen or a $C_{1-4}$alkyl group in the benzene ring; or
- $R_2$ stands for a carbamoyl group substituted by one or two $C_{1-4}$alkyl group(s) or phenyl group on the nitrogen atom which comprises a) to obtain compounds of the general formula (I) containing as $R_2$ a substituent different from an N-substituted carbamoyl group reacting a compound of the general formula (II),

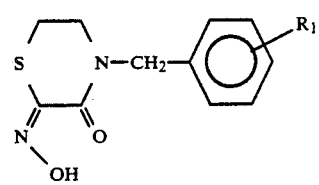

(II)

wherein $R_1$ is as defined above, in an inert organic solvent in the presence of an inorganic or organic base with a compound of the general formula (III),

 (III)

wherein $R_3$ has the same meaning as $R_2$, except the N-substituted carbamoyl group and X is halogen or, when the meaning of $R_3$ is different from an acylatable group, X may be also a mesyloxy or tosyloxy group; or b) to obtain compounds of the general formula (I) containing an N-substituted cabamoyl group as $R_2$, reacting a compound of the general formula (II), wherein $R_1$ is as defined above, in an inert organic solvent in the presence of an organic tertiary amine, preferably triethylamine with a compound of the general formula (IV),

 (IV)

wherein $R_4$ stands for a phenyl or $C_{1-4}$alkyl group.

The preparation of the 2,3-thiomorpholinedione-2-oxime derivatives of general formula (II) used as starting substances has been described in our patent application simultaneously filed. According to those reported in that patent application, the compounds of the general formula (II) can be prepared e.g. by reacting an appropriately substituted 2-nitromethylene-3-(phenylmethyl)-thiazolidine with a basic reagent in an aqueous and/or alcoholic medium.

From the 2,3-thiomorpholinedione-2-oxime derivatives of the general formula (II), the compounds according to the present invention can be prepared by the methods discussed hereinafter:

a) a substitution alkylation or acylation is carried out the using a compound of the general formula (III), wherein $R_3$ is the same as $R_2$, except any N-substituted cabamoyl group; and b) an addition acylation is performed by using a compound of the general formula (IV); in this case $R_2$ stands for an N-substituted cabamoyl group.

In the process variant a) of the present invention, the reaction is usually carried out in an organic solvent, preferably in methanol, ethanol, acetone or in an ether-type solvent, such as dioxane; or in acetonitrile, dimethylformamide or dimethylsulfoxide. Alkaline metal hydroxides, carbonates, alkoxides or organic bases such as tertiary amines may be used as acid binding agents. The reaction is usually carried out at a temperature corresponding to the boiling point of the solvent used. After filtering off the precipitated salt, the product is isolated by evaporating the reaction mixture and then purified by a method known per se.

When using process variant b) of the invention, the reaction is accomplished in the presence of a solvent and a catalyst. Depending on the solubility conditions of the reactants used, $C_{3-6}$ketones, $C_{2-5}$ethers, dimethylformamide, dimethylsulfoxide, $C_{5-10}$hydrocarbons or chlorinated hydrocarbons may preferably be employed as solvents. Suitable catalysts are organic tertiary amine bases, preferably triethylamine. The reaction temperature may be varied between 0° C. and 100° C.

Out of the compounds of the general formula (I), 4-phenylmethyl-O-methyl-2,3-thiomorpholinedione-2-oxime exerts a particularly advantageous effect based on the pharmacological inventigations. This compound shows a gastric acid secretion-inhibiting action with an oral $ED_{50}$ value of 20 mg/kg in the so-called Shay's rats, is effective also against stress-induced ulcers with an oral $ED_{50}$ value of 71 mg/kg and against acidic ethanol-induced gastric ulcers with an oral $ED_{50}$ value of 7 mg/kg.

The invention is illustrated in detail by the following non-limiting Examples.

EXAMPLE 1

General Example for the Substitution Alkylation or Acylation, Respectively

After weighing 100 mmol of a compound of the general formula (II), 20 ml of acetone, 10 mmol of a compound of the general formula (III), 10 mmol of potassium carbonate and 1 mmol of potassium iodide in a round-bottom flask, the reaction mixture is refluxed until the substance of general formula (II) as detected by thin layer chomatograhy (TLC) diappears, then the inorganic precipitate is filtered off and the filtrate is evaporated. The residue is purified after having been solidified by adding ether by recrystallisation or by column chomatography. The data of compounds obtained by this method are summarized in Table I. Chemical names of the compounds listed in Table I:

1. 4-Phenylmethyl-O-phenylmethyl-2,3-thiomorpholinedione-2-oxime
2. 4-Phenylmethyl-O-ethoxycarbonylmethyl-2,3-thiomorpholinedione-2-oxime
3. 4-Phenylmethyl-O-methyl-2,3-thiomorpholinedione-2-oxime
4. 4-Phenylmethyl-O-ethyl-2,3-thiomorpholinedione-2-oxime
5. 4-Phenylmethyl-O-n-propyl-2,3-thiomorpholinedione-2-oxime
6. 4-Phenylmethyl-O-(3-phenyl-1-propyl)-2,3-thiomorpholinedione-2-oxime
7. 4-Phenylmethyl-O-cyanomethyl-2,3-thiomorpholinedione-2-oxime
8. 4-(2-Chlorophenylmethyl)-O-methyl-2,3-thiomorpholinedione-2-oxime
9. 4-(4-Methoxyphenylmethyl)-O-methyl-2,3-thiomorpholinedione-2-oxime
10. 4-(3-Chlorophenylmethyl)-O-methyl-2,3-thiomorpholinedione-2-oxime
11. 4-(4-Methylphenylmethyl)-O-methyl-2,3-thiomorpholinedione-2-oxime
12. 4-Phenylmethyl-O-cinnamyl-2,3-thiomorpholinedione-2-oxime
13. 4-Phenylmethyl-O-tosyl-2,3-thiomorpholinedione-2-oxime
14. 4-Phenylmethyl-O-phenylsulfonyl-2,3-thiomorpholinedione-2-oxime
15. 4-Phenylmethyl-O-(4-fluorophenylsulfonyl)-2,3-thiomorpholinedione-2-oxime
16. 4-Phenylmethyl-O-dimethylcarbamoyl-2,3-thiomorpholinedione-2-oxime
17. 4-Phenylmethyl-O-(3-hydroxy-1-propyl)-2,3-thiomorpholinedione-2-oxime

EXAMPLE 2

General Example for the Addition Acylation

After weighing 10 mmol of the compound of general formula (I), 20 ml of acetone, 15 mmol of triethylamine and 11 mmol of the substance of general formula (IV) in a round-bottom flask, the reaction mixture is stirred at room temperature for 24 hours, then the unreacted compound of the general formula (II) is filtered off and the filtrate is evaporated. The residue is purified after having been solidified by adding ether and then by recrystallisation or by direct chromatography. The data of compounds obtained by this method are summarized in Table II.

Chemical names of the compounds listed in Table II:

1. 4-Phenylmethyl-O-n-butylcarbamoyl-2,3-thiomorpholinedione-2-oxime
2. 4-Phenylmethyl-O-phenylcarbamoyl-2,3-thiomorpholinedione-2-oxime
3. 4-Phenylmethyl-O-ethylcarbamoyl-2,3-thiomorpholinedione-2-oxime

EXAMPLE 3

Preparation of 4-phenylmethyl-2,3-thiomorpholinedione-2-oxime 2.36 g (0.01 mol) of 3-phenylmethyl-2-nitromethylenethiazolidine are boiled under reflux in the mixture of 50 ml of 1N sodium hydroxide solution and 25 ml of ethanol until the dissolution of the starting substance (when, based on the TLC examination, no starting substance is detected in a sample taken from the reaction mixture). Then, the mixture is cooled, acidified by adding hydrochloric acid diluted to 1:1 with water (to a pH value of 1), the precipitated product is filtered off, washed with water and dried to give the title compound in a yield of 2,15 g (91%), m.p.: 225°-227° C.

The purity of this product is 99.7% when measured by titration with alkaline metal hydroxide in pyridine, in the presence of silver nitrate.

TABLE I

| No. | Reactant | $R_1$ | $R_3$ | Reaction time hour | Yield % | Melting point °C. | IR spectrum | NMR spectrum |
|---|---|---|---|---|---|---|---|---|
| 1 | Benzyl bromide | H | Ph—CH$_2$— | 2 | 59.2 | 103 /EtOH/ | 1657 1015 | 2.8/m, 2H, CH$_2$/ 3.6/m, 2H, CH$_2$/ 4.6/s, 2H, CH$_2$/ 5.3/s, 2H, CH$_2$/ 7.2/2×s, 20H, ArH/ |
| 2 | Ethyl bromoacetate | H | —CH$_2$—CO$_2$Et | 8 | 45 | 109–110 /EtOH/ | 1750 1660 1220 1065 | 1.3/t, 3H, CH$_3$/ 2.9/m, 2H, CH$_2$/ 3.7/m, 2H, CH$_2$/ 4.3/q, 2H, CH$_2$/ 4.8/s, 2H, CH$_2$/ 5.0/s, 2H, CH$_2$/ 7.4/s, 5H, ArH/ |
| 3 | Methyl iodide | H | —CH$_3$ | 4 | 57 | 95–96 /i-PrOH/ | 1645 1030 | 2.8/m, 2H, CH$_2$/ 3.7/m, 2H, CH$_2$/ 4.2/s, 3H, CH$_3$/ 4.8/s, 2H, CH$_2$/ 7.4/s, 5H, ArH/ |
| 4 | Ethyl iodide | H | —C$_2$H$_5$ | 6 | 52 | 86–88 /50% EtOH/ | 1648 1045 | 1.4/t, 3H, CH$_3$/ 2.9/m, 2H, CH$_2$/ 3.7/m, 2H, CH$_2$/ 4.5/q, 2H, CH$_2$/ 4.8/s, 2H, CH$_2$/ 7.4/s, 5H, ArH/ |
| 5 | n-Propyl bromide | H | n-C$_3$H$_7$ | 6 | 30.6 | 49–50 /chrom/ | 1650 960 | 0.9/t, 3H, CH$_3$/ 1.7/m, 2H, CH$_2$/ 2.8/m, 2H, CH$_2$/ 3.6/m, 2H, CH$_2$/ 4.3/t, 2H, CH$_2$/ 4.7/s, 2H, CH$_2$/ 7.3/s, 5H/ |
| 6 | 3-Phenylpropyl bromide | H |  | 24 | 71 | 81–82 /chrom/ | 1656 981 | 2.0/m, 2H, CH$_2$/ 2.7/t, 2H, CH$_2$/ 2.8/m, 2H/ 3.6/m, 2H, CH$_2$/ 4.3/t, 2H, CH$_2$/ 4.7/s, 2H, CH$_2$/ 7.2/ArH/ |
| 7 | Chloroacetonitrile | H |  | 5 | 41.4 | 77–79 /i-PrOH/ | 1655 1018 | 3.0/m, 2H, CH$_2$/ 3.8/m, 2H, CH$_2$/ 4.8/s, 2H, CH$_2$/ 5.0/s, 2H, CH$_2$/ 7.4/s, 5H, ArH/ |
| 8 | Methyl iodide | 2-Cl | CH$_3$ | 4 | 70.2 | 128–129 /i-PrOH/ | 1650 /broad/ 1030 2840 | 3.0/m, 2H, CH$_2$/ 3.7/m, 2H, CH$_2$/ 4.1/s, 3H, CH$_3$/ 4.8/s, 2H, CH$_2$/ 7.3/s, 5H, ArH/ |
| 9 | Methyl iodide | 4-OCH$_3$ | CH$_3$ | 4 | 46.7 | 107–110 /i-PrOH/ | 1650 1020 2840 | 2.9/q, 2H, CH$_2$/ 3.6/q, 2H, CH$_2$/ 3.8/s, 2H, CH$_2$/ 4.2/s, 3H, CH$_3$/ |

TABLE I-continued

| No. | Reactant | $R_1$ | $R_3$ | Reaction time hour | Yield % | Melting point °C. | IR spectrum | NMR spectrum |
|---|---|---|---|---|---|---|---|---|
| 10 | Methyl iodide | 3-Cl | CH$_3$ | 3 | 65.1 | 79–81 /chrom/ | 1645 2830 1028 | 4.6/s, 3H, CH$_3$/ 7.0/q, 4H, ArH/ 2.9/m, 2H, CH$_2$/ 3.7/m, 2H, CH$_2$/ 4.2/s, 2H, CH$_2$/ 4.7/s, 2H, CH$_2$/ 7.3/s, 5H, ArH/ |
| 11 | Methyl iodide | 4-CH$_3$ | CH$_3$ | 3 | 54.6 | 93–95 /chrom/ | 1638 1038 2830 | 2.3/s, 3H, CH$_3$/ 2.9/m, 2H, CH$_2$/ 3.7/m, 2H, CH$_2$/ 4.2/s, 2H, CH$_2$/ 4.7/s, 2H, CH$_2$/ 7.2/s, 5H, ArH/ |
| 12 | Cinnamyl chloride | H | –CH$_2$–CH=CH–Ph | 24 | 71.2 | 115–116 /CH$_3$CN/ | 1645 978 985 | 2.8/m, 2H, CH$_2$/ 3.6/m, 2H, CH$_2$/ 4.7/s, 2H, CH$_2$/ 5.0/d, 2H, CH$_2$/ 6.5/m, 2H, CH=CH/ 7.3/s, 10H, ArH/ |
| 13 | Tosyl chloride | H | –SO$_2$–C$_6$H$_4$–CH$_3$ | 24 | 46.9 | 166–167 /ethylacetate/ | 1660 1377 1180 | 2.4/s, 3H, CH$_3$/ 2.8/m, 2H, CH$_2$/ 3.7/m, 2H, CH$_2$/ 4.7/s, 2H, CH$_2$/ 7.3/s, 5H, ArH/ 7.6/qc, 4H, ArH/ |
| 14 | Benzenesulfonyl chloride | H | –SO$_2$–C$_6$H$_5$ | 5 | 61.5 | 121–123 /chrom/ | 1660 1180 820 | 2.9/m, 2H, CH$_2$/ 3.7/m, 2H, CH$_2$/ 4.6/s, 2H, CH$_2$/ 7.3/s, 5H, ArH/ 7.4–8.1/m, 5H, ArH/ |
| 15 | 4-Fluorobenzenesulfonyl chloride | H | –SO$_2$–C$_6$H$_4$–F | 12 | 91 | 115–116 /i-PrOH/ | 1650 1190 | 2.9/m, 2H, CH$_2$/ 3.7/m, 2H, CH$_2$/ 4.7/s, 2H, CH$_2$/ 7.2/d, 2H, ArH/ 7.3/s, 5H, A H/ 8.1/2×d, 2H, ArH/ |
| 16 | Dimethylcarbamoyl chloride | H | –C(=O)–N(CH$_3$)$_2$ | 3 | 69.4 | 150–152 | 1740 1665 1150 | 3.0/s+m, 8H, CH$_2$+CH$_3$/ 3.7/m, 2H, CH$_2$/ 4.8/s, 2H, CH$_2$/ 7.4/s, 5H, ArH/ |
| 17 | 3-Chloro-1-propanol | H | –CH$_2$–CH$_2$–CH$_2$–OH | 24 | 22 | 59–60 | 3450 1040 1650 1057 | 1.9/q, 2H, CH$_2$/ 2.8/m, 2H, CH$_2$/ 3.6/m, 2H, CH$_2$/ 4.5/t, 2H, CH$_2$/ 4.7/s, 2H, CH$_2$/ 7.3/s, 5H, Ar/ |

TABLE II

| No | Reaction | $R_1$ | $R_4$ | Reaction time, hour | Yield % | Melting point °C | IR spectrum | NMR spectrum |
|---|---|---|---|---|---|---|---|---|
| 1 | Butylisocyanate | H | nBu | 24 | 73 | 99–100 /ethylacetate/ | 1765<br>1655<br>3350<br>970 | 0.9/t,3H,CH$_2$/<br>1.4/m,4H,2CH$_2$/<br>2.9/m,2H,CH$_2$/<br>3.3/q,2H,CH$_2$/<br>3.7/m,2H,CH$_2$/<br>4.7/s,2H,CH$_2$/<br>7.4/s,5H,ArH/<br>6.7/t,1H,NH/ |
| 2 | Phenylisocyanate | H | Ph | 24 | 66 | 169–170 /ethylacetate/ | 1750<br>1662<br>3280<br>960 | 3.0/m,2H,CH$_2$/<br>3.7/m,2H,CH$_2$/<br>4.7/s,2H,CH$_2$/<br>7.1–7.7/m+s,10H,ArH/<br>8.7/b*,1H,NH/ |
| 3 | Ethylisocyanate | H | C$_2$H$_5$ | 24 | 24.8 | 110–112 /chrom/ | 1760<br>1658<br>3340<br>1230 | 1.2/t,3H,CH$_3$/<br>2.9/m,2H,CH$_2$/<br>3.3/q,2H,CH$_2$/<br>3.7/b,2H,CH$_2$/<br>4.7/s,2H,CH$_2$/<br>6.6/b*,1H,NH/<br>7.3/s,5H,ArH/ |

We claim:

1. A 2,3-Thiomorpholinedione-2-oxime derivative of the formula (I),

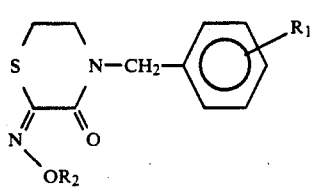

wherein

R$_1$ stands for hydrogen, halogen, C$_{1-4}$alkyl, C$_{1-4}$alkoxy or nitro group;

R$_2$ means a C$_{1-7}$alkyl group optionally substituted by: a hydroxyl or oxo group; or an ester group containing 1 to 4 carbon atoms in the alkoxy moiety; or a C$_{1-4}$alkoxy, cyano, amino, C$_{1-4}$alkylamino, or dialkylamino group; or an acyl group containing 1 to 7 carbon atoms in the alkyl moiety; or R$_2$ means an aryl-C$_{1-7}$alkyl group optionally bearing the substituents defined above for R$_2$ in the alkyl chain and optionally substituted by halogen, nitro, C$_{1-4}$alkyl or alkoxy group in the benzene ring; or R$_2$ represents an allyl, phenylallyl or phenylsulfonyl group, both latter groups optionally being substituted by halogen or a C$_{1-4}$alkyl group in the benzene ring; or R$_2$ stands for a carbamoyl group substituted by one or two C$_{1-4}$alkyl group(s) or phenyl group on the nitrogen atom.

2. 4-Phenylmethyl-O-methyl-2,3-thiomorpholinedione-2-oxime.

3. A pharmaceutical composition, which comprises as active ingredient an anti-ulcer effective amount of a 2,3-thiomorpholinedione-2-oxime derivative of the formula (I),

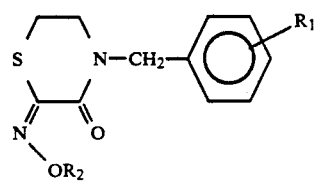

wherein

R$_1$ stands for hydrogen, halogen, C$_{1-4}$alkyl, C$_{1-4}$alkoxy or nitro group;

R$_2$ means a C$_{1-7}$alkyl group optionally substituted by: a hydroxyl or oxo group; or an ester group containing 1 to 4 carbon atoms in the alkoxy moiety; or a C$_{1-4}$alkoxy, cyano, amino, C$_{1-4}$alkylamino, or dialkylamino group; or an acyl group containing 1 to 7 carbon atoms in the alkyl moiety; or R$_2$ means an aryl-C$_{1-7}$alkyl group optionally bearing the substituents defined above for R$_2$ in the alkyl chain and optionally substituted by halogen, nitro, C$_{1-4}$alkyl or alkoxy group in the benzene ring; or R$_2$ represents an allyl, phenylallyl or phenylsulfonyl group, both latter groups optionally being substituted by halogen or a C$_{1-4}$alkyl group in the benzene ring; or R$_2$ stands for a carbamoyl group substituted by one or two C$_{1-4}$alkyl group(s) or phenyl group on the nitrogen atom in admixture with inert carriers and/or additives commonly used in the pharmaceutical industry.

* * * * *